United States Patent
Latypov

(10) Patent No.: US 6,275,770 B1
(45) Date of Patent: Aug. 14, 2001

(54) METHOD TO REMOVE STATION-INDUCED ERROR PATTERN FROM MEASURED OBJECT CHARACTERISTICS AND COMPENSATE THE MEASURED OBJECT CHARACTERISTICS WITH THE ERROR

(75) Inventor: Azat M. Latypov, Danbury, CT (US)

(73) Assignee: IPEC Precision Inc., Bethel, CT (US)

( * ) Notice: Subject to any disclaimer, the term of this patent is extended or adjusted under 35 U.S.C. 154(b) by 0 days.

(21) Appl. No.: 09/321,034

(22) Filed: May 27, 1999

(51) Int. Cl.$^7$ .................................................. G01N 21/00
(52) U.S. Cl. ............................................ 701/168; 702/159
(58) Field of Search ................................ 702/33, 35, 36, 702/81, 82, 83, 84, 85, 90, 91, 94, 95, 150, 155, 159, 167–168

(56) References Cited

U.S. PATENT DOCUMENTS

| | | | |
|---|---|---|---|
| 4,748,335 | * 5/1988 | Lindow et al. | 250/559.22 |
| 4,750,141 | 6/1988 | Judell et al. | . |
| 4,805,123 | * 2/1989 | Specht et al. | 382/144 |
| 4,860,229 | 8/1989 | Abbe et al. | . |
| 4,931,962 | 6/1990 | Palleiko | . |
| 5,481,483 | * 1/1996 | Ebenstein | 364/561 |
| 5,546,179 | * 8/1996 | Cheng | 356/73 |
| 5,642,298 | 6/1997 | Mallory et al. | . |
| 5,864,394 | * 1/1999 | Jordon, III et al. | 356/237.2 |

FOREIGN PATENT DOCUMENTS

09260252 * 3/1997 (JP).

OTHER PUBLICATIONS

IPEC Precision *Acuflat Wafer Thickness Mapper User Manual* rev. Oct. 21, 1997.
Standard Test Method for Measuring Flatness, Thickness, and Thickness Variation on Silicon Wafers by Automated Noncontact Scanning, ASTM Designation F 1530–94, 1994, pp. 610–615.

* cited by examiner

Primary Examiner—Kamini Shah
Assistant Examiner—Craig Miller
(74) Attorney, Agent, or Firm—Snell & Wilmer L.L.P.

(57) ABSTRACT

In the measurement of the surface of a wafer mounted on a mounting device, a method of removing the errors induced by the mounting device from the measurement data. The method includes the steps of 1) measuring a plurality of points on the surface to obtain a first matrix which contains the device induced errors and the proper surface of the object; 2) rotating the object independently of the mounting device; 3) measuring the rotated object to obtain a second matrix which contains the device induced errors and the proper surface of the object as transformed by a rotation matrix; 4) obtaining the difference of the second matrix and the first matrix thereby eliminating the device induced error; and 5) applying the inverses of LU matrices on the difference of the rotation matrix and an identity matrix to obtain the proper surface. In step 5, the process involves flipping the wafer and measuring the surface as flipped.

15 Claims, 4 Drawing Sheets

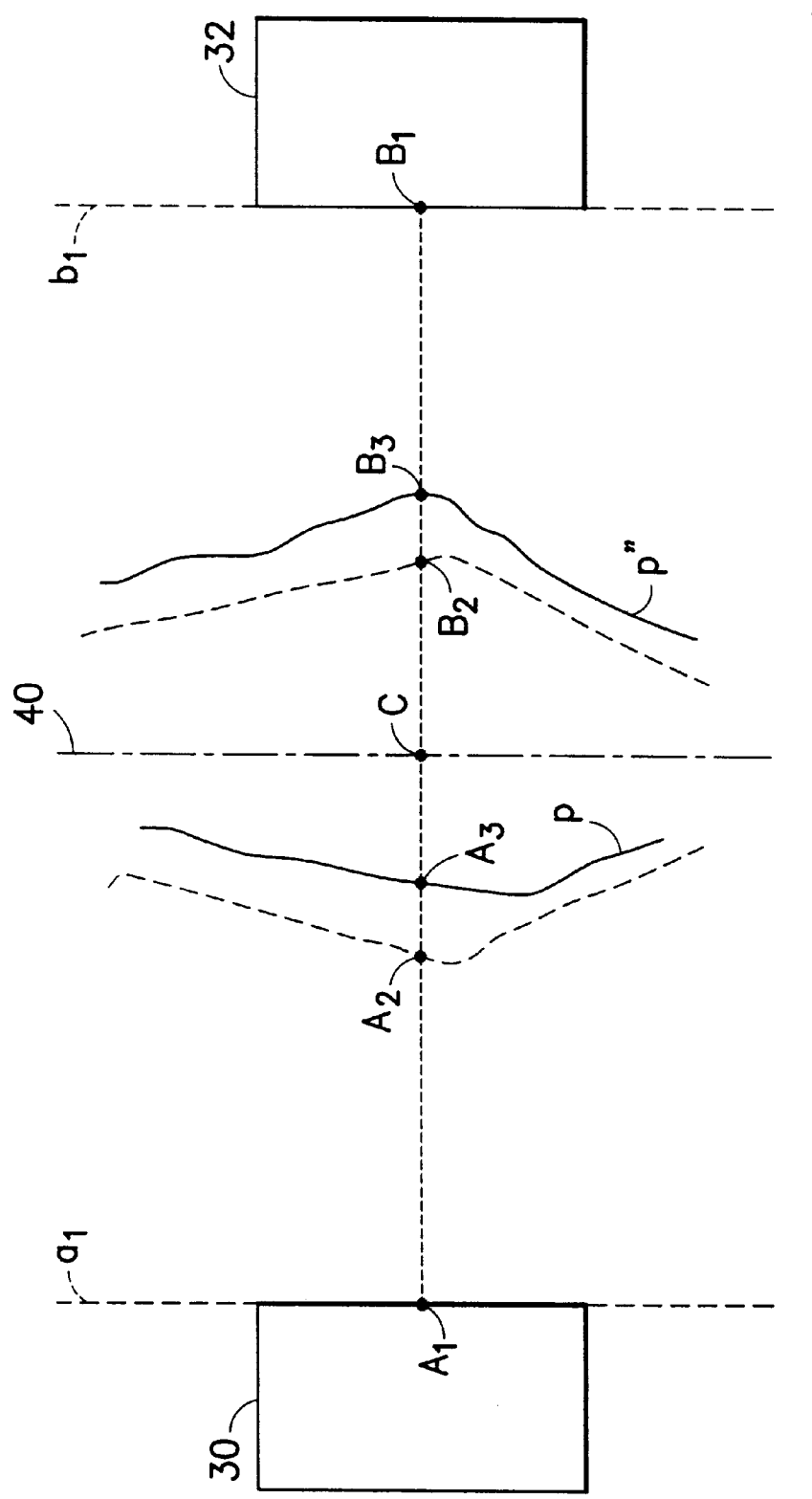

METHOD TO REMOVE STATION-INDUCED ERROR PATTERN FROM MEASURED OBJECT CHARACTERISTICS AND COMPENSATE THE MEASURED OBJECT CHARACTERISTICS WITH THE ERROR

BACKGROUND OF THE INVENTION

1. Field of the Invention

The present invention relates generally to the measurement of semiconductor wafers and, more specifically, to a pattern recognition methodology implemented in a semiconductor wafer measurement station for removing station induced error from measured object characteristics.

2. Background of the Invention

During the many phases of the integrated circuit fabrication process, it is useful to know the surface characteristics of the semiconductor wafers, especially the bow and warp of the wafers. One of the most difficult aspect of the measurement is the separation of the station or fixture-induced errors from the measurement data. As disclosed in U.S. Pat. No. 4,750,141 (Judell et al.), fixture-induced errors can be removed by performing Fourier Transform on the measurements of a wafers at different orientations. The major disadvantages of the measurement method as disclosed in Judell et al are as follows:

1. Even with the use of the Fast Fourier-Transform (FFT) technique, FT is, nonetheless, a procedure that requires either computing trigonometric functions for each act of the calculation of the FT, or storing the computed Fourier basis in the memory, resulting in a larger flop count or larger memory requirements.

2. The noise reduction through computing a weighted average of two solutions requires taking additional measurement of the rotated wafer, and.

3. It does not provide means to compensate for the tilt that may occur because the wafer surface touching the chuck is not flat.

It is, therefore, desirable to provide a method for measuring the surface characteristics of a semiconductor wafer and removing the fixture, or station-induced errors from the measurement without using the Fourier-Transform methodology and taking additional measurement of the rotated wafer for noise reduction.

SUMMARY OF THE INVENTION

The present invention provides a method of measuring the surface profile of an object to develop a surface profile map for the object's surface without station-induced errors, the method comprises the steps of:

1) providing an object having a surface whose profile is to be measured;
2) providing a measurement device having an object holder, a first distance sensor and a second distance sensor spaced apart from the first distance sensor by a known distance;
3) holding the object with the object holder in a first orientation with respect to the object holder;
4) disposing the object in the first orientation with respect to the object holder between the first and second distance sensors so that the object's surface is facing the first distance sensor;
5) measuring the distance between the first distance sensor and the object's surface in the first orientation with respect to the object holder for a plurality of points over the object's surface in a first coordinate pattern of known orientation with respect to the object holder to obtain a first matrix of measurement points;
6) rotating the object about a first axis which is substantially normal to the object's surface so as to hold the object with the object holder in a second orientation with respect to the object holder, wherein said rotation is represented by a rotation matrix;
7) disposing the object in the second orientation with respect to the object holder between the first and second distance sensors so that the object's surface is facing the first distance sensor;
8) measuring the distance between the first distance sensor and the object's surface in the second orientation with respect to the object holder for a plurality of points over the object's surface in second coordinate pattern of known orientation with respect to the object holder to obtain a second matrix of measurement points;
9) obtaining a difference matrix by subtracting the first matrix from the second matrix;
10) removing the rotation matrix by applying an inverse matrix to the difference matrix, wherein the inverse matrix is the inverse of difference between the rotation matrix and an identity matrix;
11) flipping the object about a second axis which is substantially perpendicular to the first axis so as to hold the object with the object holder in a third orientation with respect to the object holder;
12) disposing the object in the third orientation with respect to the object holder between the first and second distance sensors so that object's surface is facing the second distance sensor;
13) measuring the distance between the second distance sensor and the object's surface in the third orientation with respect to the object holder for a plurality of points over the object's surface in third coordinate pattern of known orientation with respect to the object holder to obtain a third matrix of measurement points; and
14) obtaining the surface map of the object's surface by applying selected measurement points of the third matrix to the difference matrix as processed in step 10.

The present invention will become apparent upon reading the drawings and the accompanying description.

BRIEF DESCRIPTION OF THE DRAWINGS

FIG. 3 illustrates the station-induced errors in a measured distance between the surface and the measuring probe.

DETAILED DESCRIPTION OF THE INVENTION

Figure 1A:
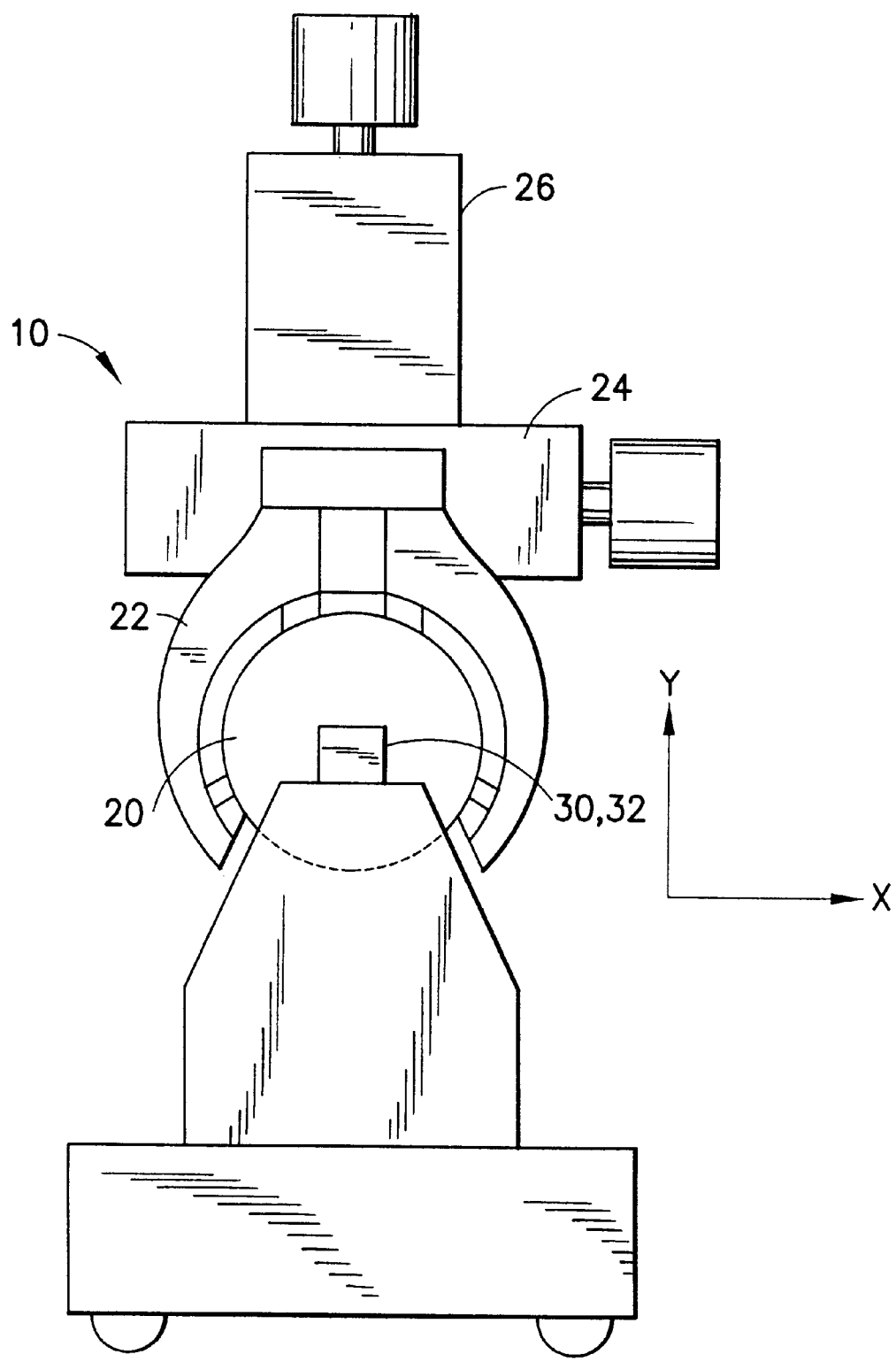
FIG. 1A and FIG. 1B illustrate a measurement device for measuring the surface of an object.

FIG. 1A illustrates a measurement device 10 for measuring the surface of an object 20. In particular, the object 20 is a semiconductor wafer. Measurement device 10 includes wafer arms 22 for holding wafer 20, preferably, in a vertical position by its edges. A pair of distance measuring probes 30, 32, preferably optical sensors, are placed on opposite sides of the wafer and facing each other along a line which is substantially perpendicular to the wafer surface. Device 10 is also equipped with an X-translation stage 24 and a Y-translation stage 26 so as to move the wafer about a plane substantially perpendicular to the line joining the two probes. Using these two orthogonally arranged linear translation stages, the wafer can be moved with respect to the probes so that the distance measurement between the wafer surface and the probes can be obtained for a plurality of nodes on a rectangular or square measurement grid (in Cartesian coordinates). However, in order to simplify the processing of the measurement data, it is preferred that the distance measurements in Cartesian coordinates be mapped into polar coordinates using interpolation and/or extrapolation of data points. Alternatively, the device can be programmed to make distance measurements on a plurality of nodes arranged in concentric circles (a polar grid).

Figure 1B:
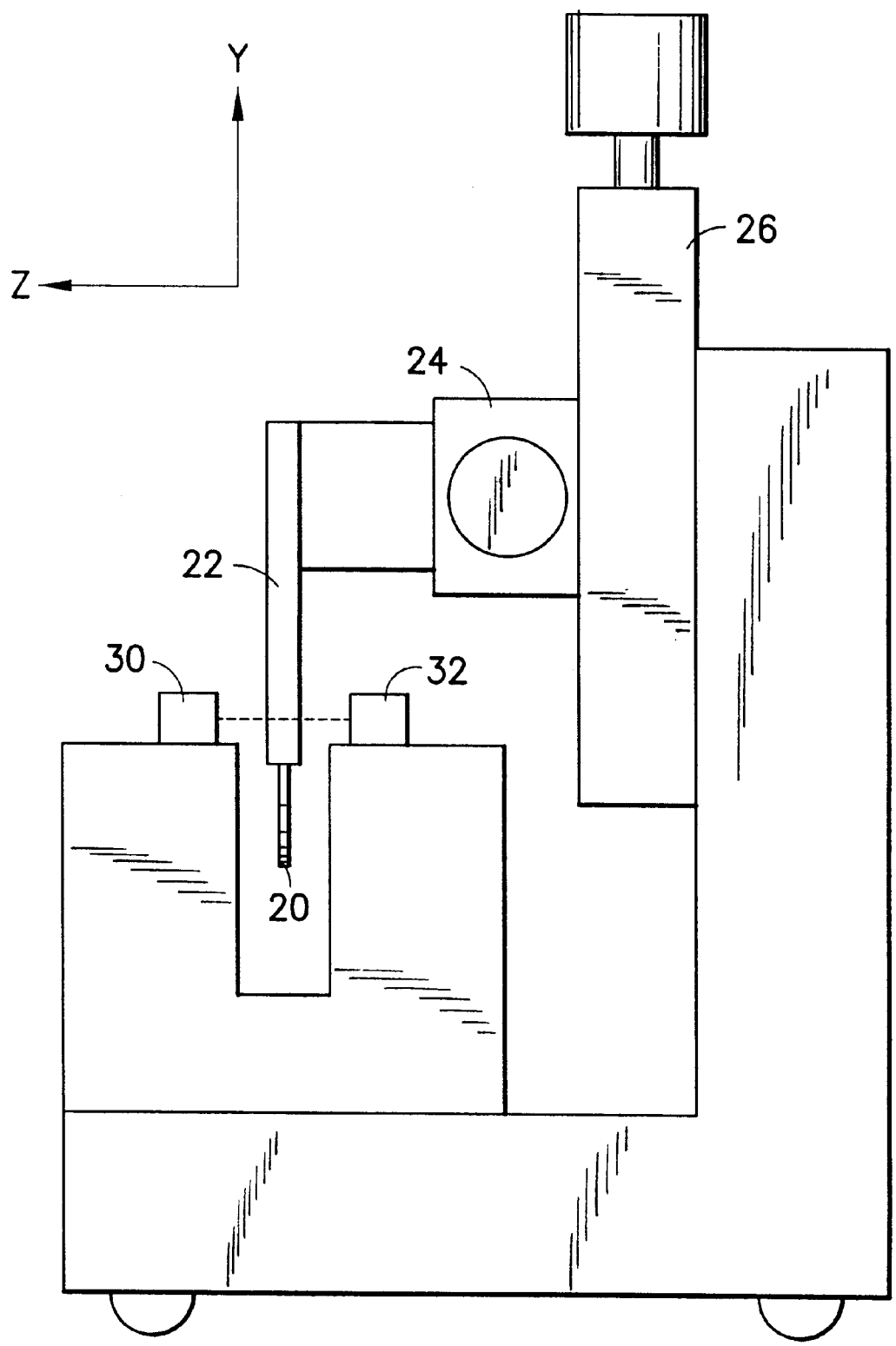

FIG. 1B illustrates another view of the same measurement device. It should be noted that the device for measuring the wafer surface as shown in FIGS. 1A and 1B is for illustrative purposes only. The method of removing station-induced errors from measurement data of an object, according to the present invention, is equally applicable to measurement data taken from a device in which the measuring probes are moved to different positions while the wafer is keep stationary. Furthermore, the method is also applicable to measurement data taken in a device wherein the wafer can be rotated along with the wafer mount in relation to the probes.

Figure 2A:
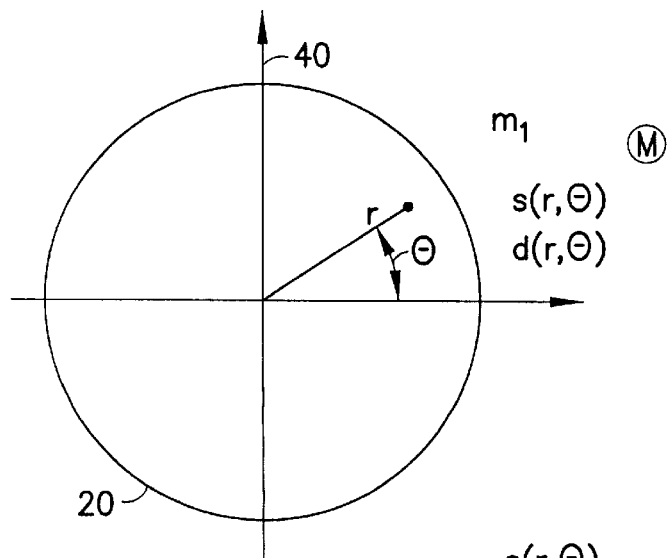
FIGS. 2A through 2C illustrate a measuring point of the surface at different orientations.
Figure 2B:
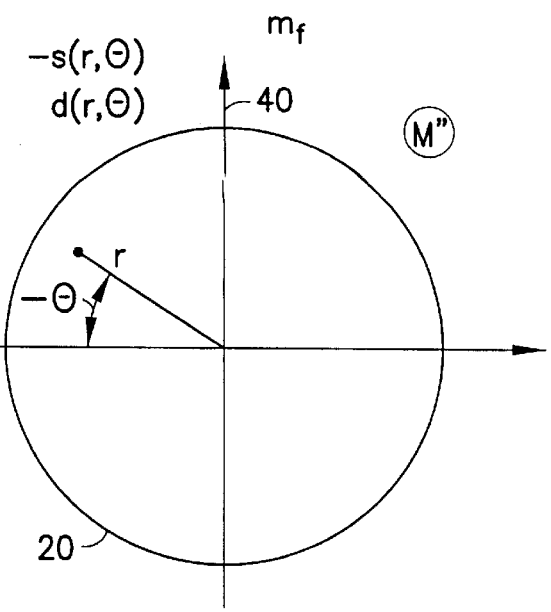
Figure 2C:
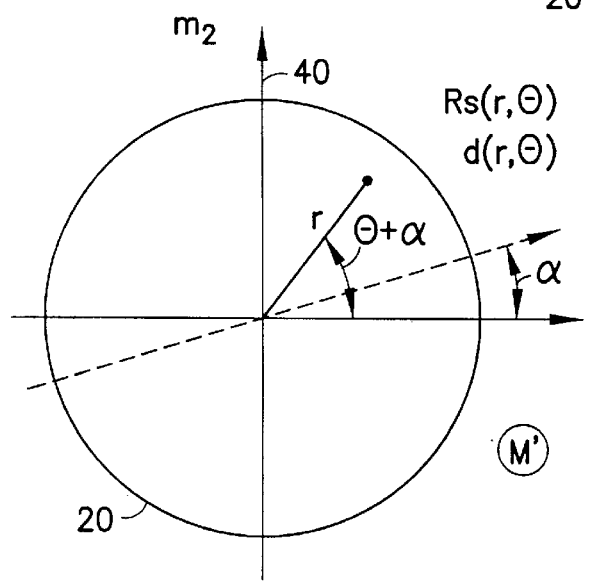

FIGS. 2A through 2C illustrate a measurement point of the surface at different orientations. As shown in FIG. 2A, a point $(r,\theta)$ on wafer 20, in relation to a first axis 40 is measured by first sensor 30 while wafer 20 is held in the wafer arms 22 (FIG. 1B). At this first orientation, a plurality of points are measured, mapped into polar coordinates, and represented by a first matrix M, which contains the proper shape of the surface S and the station-induced errors E, as shown in Eq.1 below.

FIG. 2B illustrates the wafer being flipped about a flip line 40 by 180 degrees. The first surface of the object as flipped is measured by second sensor 32 (FIG. 1B). In polar coordinates, the measured points are represented by a third matrix M". For the nodes along the flip line 40, the third matrix M" contains the proper shape of the surface map matrix S and the station-induced errors $-E$ (see FIG. 3). The purpose of making measurements on the flipped wafer is to independently determine the value of components in the surface map matrix S along the flip line, as shown in FIG. 3.

FIG. 2C illustrates the wafer being rotated by an angle $\alpha$ independently of the wafer arms. This means that, after the wafer surface is measured to obtain the first matrix M, it is taken out of the wafer arms and rotated by an angle $\alpha$. The rotated wafer is put back on the wafer arms and the wafer surface is again measured to obtain the second matrix M'.

The method of removing station-induced errors from measurement data of an object using a device for holding the measured object, according to the present invention, can be summarized in the following steps:

In step 1, a multiplicity of measurement points on the object's surface are measured by the first sensor to form an $N_x \times N_y$ matrix, the entries of which represent the measured distance from the first sensor to the object's surface at the nodes of a rectangular or square measurement grid (a Cartesian grid). In order to simplify the processing of measurement data, the entries in the matrix are mapped into polar coordinates. From the mapped measurement data, select a plurality of entries to form a first matrix M contains a surface map matrix S and a station-induced error matrix E, or $$M = S + E \qquad (1)$$

In general, M, S and E can be chosen as matrices having a dimension of $N_\theta \times N_r$. As such, Equation 1 represents a system of $N_r \times N_\theta$ equations. In order to further simplify the computation, instead of solving $N_r \times N_\theta$ equations, it is preferable to solve $N_r$ independent systems of $N_\theta$ equations. Thus, it is preferred that the first matrix M contains measurement data sampled only at the nodes of the polar grid with a certain first radius and matrix M is a column matrix having a dimension of $N_\theta \times 1$, or a vector of length $N_\theta$. Each vector M is one column of an $N_\theta \times N_r$ matrix. Accordingly, the surface map matrix S and the station-induced error matrix E are also column matrices of the same dimension or vectors of the same length.

In step 2, the measured object is rotated about a first axis which is substantially parallel to the object's surface by an angle $\alpha$ to place the measured object at a second orientation. The rotation is represented by an $N_\theta \times N_\theta$ rotation matrix R. In polar coordinates, this matrix has a simple form of a "periodic shift" matrix. If the main diagonal of R is assigned the number 0 and all diagonals above the main diagonal are assigned consecutive numbers from 1 to $N_\theta - 1$, and all diagonals below the main diagonal are assigned the numbers from $-1$ to $-(N_\theta - 1)$, then the rotation matrix R, corresponding to the rotation which results in a shift of H segments of polar grid in angular direction, can be described as a matrix with 1's on its $-H$ and $N_\theta - H$ diagonals and zeros everywhere else.

In step 3, a multiplicity of second points on the first surface of the measured object at the second orientation are measured by the first sensor to obtain another matrix of entries, representing the distance from the first sensor to the rotated object's surface at the same nodes of the Cartesian grid as used in step 1. Similarly, the entries in this matrix are mapped into polar coordinates to form a second matrix M' which contains the same station-induced error matrix E and a surface map matrix S transformed by the rotation matrix R, or $$M' = RS + E \qquad (2)$$

As with M in step 1, it is preferred that the second matrix M' contains measurement data sampled at the nodes of the polar grid with the same first radius. Thus, the matrix M' is a column matrix having a dimension of $N_\theta \times 1$, or a vector of length $N_\theta$.

In step 4, the station-induced errors E is separated from the measurements by subtracting the first matrix from the second matrix. The difference of the second matrix M' and the first matrix M is the surface map matrix S transformed by a difference matrix which is the difference of the rotation matrix R and an identity matrix I, or $$(R-I)S = M' - M \qquad (3)$$

It should be noted that Equation represents is a rank-deficient system of $N_\theta$ linear equations for $N_\theta$ unknown elements of S. By choosing the angle of rotation $\alpha$ appropriately, the rank of the matrix $R-I$ can be made to be equal to $N_\theta - 1$. One way to achieve that is to choose $\alpha$ such that the fraction $H/N_\theta$ is an irreducible fraction. After the angle $\alpha$ is chosen in that way, in order for Eq.3 is be compatible, its right-hand side must be orthogonal to the null-space of the transpose of $(R-I)$. Because the basis of the null space consists of only one vector with all its components being 1, this compatibility condition reduces to $$\Sigma(M' - M) = 0. \qquad (4)$$

Ideally, the right-hand side satisfies this condition automatically because M' and M are each a sum of a deformation a (rotated) proper shape. Therefore, the sum of components in these vectors must be the same. In reality, because of the small measurement and interpolation errors, Eq.4 is never satisfied exactly and Eq.3 is an incompatible system.

In order to make the system as described by Eq.3 compatible, it is modified by subtracting a mean of the vector M'−M (a small correction) from all components of the right-hand side.

In the next step, the difference matrix of Eq.3 is removed from the surface map. The difference matrix is LU decomposed, where L and U are, respectively, the lower triangular matrix and the upper triangular matrix, or $$LU=R-I \quad (5)$$

Because Eq.3 is a rank-deficient system of liner equations, the rank of (R−I) is less than the dimension of the matrix itself. Therefore, the last row in U is composed of zeros. Accordingly, the upper triangular matrix can be partitioned as follows:

$$U = \begin{bmatrix} u_1 & U_r \\ 0 & 0 \end{bmatrix} \quad (6)$$

where $u_1$ is the first column of U without the last (zero) entry, and $U_r$ contains the remaining entries of the matrix U.

It should be noted that, in Eq.3, the only unknown matrix is the surface map matrix S, with $N_\theta$ unknown elements of S. As (R−I) is LU decomposed and L is known, it can be assigned such that:

$$\lambda = L^{-1}(M'-M) \quad (7)$$
$$= US$$

where $\lambda$ is referred to as an auxiliary matrix.

In order to independently determine the value of one component of S, say $s_1$, the measured object at the first orientation is flipped over (a 180 degree rotation) about a second axis substantially perpendicular to the first axis to place the object at a third orientation. A multiplicity of third points on the first surface of the measured object as flipped are measured by the second sensor to obtain a third matrix M" of entries in polar coordinates in a fashion similar to step 1 and step 3. Assuming the second axis corresponds to the value of the polar angle equal to 0 and $\pi$ and denoting $m_1$, $m"_1$, $s_1$ and $e_1$ the values of the components of M, M", S and E at one and the same node of the polar grid located on the second axis, we have $$m_1 = s_1 + e_1$$
$$m"_1 = s_{1-e1}$$

and $$s_1 = (m_1 + m"_1)/2 \quad (8)$$

With $s_1$ found above, the surface map matrix S can be partitioned as follows:

$$S=[s_1 S_r]^T \quad (9)$$

Furthermore, it is possible to partition X as follows:

$$\lambda=[\lambda_r \lambda_1]^T \quad (10)$$

where $\lambda_r$ and $S_r$ are column matrices of $N_\theta-1$ elements. It is followed that $$\begin{bmatrix} u_1 & U_r \\ 0 & 0 \end{bmatrix} \begin{bmatrix} s_1 \\ S_r \end{bmatrix} = \begin{bmatrix} \lambda_r \\ \lambda_1 \end{bmatrix} \quad (11)$$

and the first $N_\theta-1$ equations of Eq.10 can be written as $$u_1 s_1 + U_r S_r = \lambda_r \quad (12)$$

From Eq.11, the remaining components of the unknown vector ($S_r$) can be found as:

$$S_r = (U_r)^{-1}(\lambda_r - s_1 u_1) \quad (13)$$

It should be noted that, in the above-described steps, the vectors or column matrices M, M' and M" of a dimension $N_\theta \times 1$ are selected from respective matrices having a dimension $N_\theta \times N_r$. Therefore, the procedure must repeated $N_r$ times, each with the measured data sampled at the nodes of the polar grid with a different radius. With the object being measured only once at each of the three orientations: the first, second and third orientations, the solution procedure for finding S as described above is repeated $N_r$ times, each for one different concentric circle on the polar grid. However, because the object is rotated once, the same rotation matrix R is applied to any of the $N_r$ concentric circles. Accordingly, LU factorization and inversion of L and U matrices need be computed only once. For a chosen set of $N_\theta$ and H, the rotation matrix R is the same, regardless of the measurement data and the measurement station. For example, if $N_\theta=5$ and H=2, the rotation matrix is given by $$R = \begin{matrix} 0 & 0 & 0 & 1 & 0 \\ 0 & 0 & 0 & 0 & 1 \\ 1 & 0 & 0 & 0 & 0 \\ 0 & 1 & 0 & 0 & 0 \\ 0 & 0 & 1 & 0 & 0 \end{matrix} \quad (14)$$

When the data is sampled at 5 equidistant nodes positioned along a circle and these measurements are arranged in a vector with components (a1, a2, a3, a4, a5), then the product of the above matrix R and this vector will be a vector with components (a4, a5, a1, a2, a3). The rotation angle a in this particular example is $360°*H/N_\theta=144°$. In practice, it is preferable to have a higher number of shifts, H, such as 9.

Because the rotation matrix is independent not only of the measurement data but also independent of the measurement station, it can be used in any measured data set taken from any measurement station. Accordingly, the LU matrices and their inverses are also independent of the measurement data and the measurement station, so long as the spacings of the polar grid and the rotation angle remain the same. Therefore, it is possible that a series of L, U matrices and their inverses for a plurality of combinations of $N_\theta$'s and H's are pre-computed and stored in a measurement station.

With pre-computed LU and the inverses thereof stored in a measurement station, the LU decomposition of R−I as described in connection with Equations 5 through 7 is no longer necessary.

In order to further demonstrate how the proper surface S along the flip line can be obtained, an exaggerated object surface profile and an exaggerated station-induced deformation are depicted in FIG. 3. In FIG. 3, there are shown two probes 30 and 32 being used to map the proper surface S of an object. In the figure, −S denoted the proper surface as flipped about the flip line 40 by 180 degrees. P and P" denote the object's surface as deformed by the wafer mount (the station-induced errors) at the two positions, respectively. When the wafer surface is measured by probe 30, the distance between the probe 30 and the surface is given by $$m_1 = |A_1A_3| = |A_1A_2| + |A_2A_3| \quad (15)$$

where $|A_1A_2|$ is the distance between reference plane $a_1$ at probed 30 and the surface of the wafer in the absence of deformation, or station-induced errors. $|A_2A_3|$ is the deformation.

When the same surface is measured by probe 32 after the wafer is flipped, the distance is given by $$m''_1 = |B_1B_3| = |B_1B_2| - |B_2B_3| \quad (16)$$

According to Equation 8 above, $$\begin{aligned} s_1 &= (m_1 + m''_1)/2 \quad &(17)\\ &= (|A_1A_2| + |B_1B_2|)/2 \\ &= (|A_1C| - |A_2C| + |B_1C| - |B_2C|)/2 \\ &= (1/2)|A_1B_1|V - |A_2C| \end{aligned}$$

In the above equation, C is the point of intersection of $A_1B_1$ and the flip line 40 and $|A_2C|$ is assumed to equal $|B_2C|$ because the wafer is flipped. Furthermore, $$\begin{aligned} s_1 &= (1/2)|A_1B_1| - |A_2C| \quad &(18)\\ &= (1/2)|A_1B_3| - (|A_1C| - |A_1A_2|) \\ &= |A_1A_2| + \{(1/2)|A_1B_1| - |A_1C|\} \end{aligned}$$

It should be noted that the terms within the bracket { } are constant because they are related to the distance between the probes and between the flip line and a probe. Over the measurement process, only the X translation stage and the Y translation stage are used to move the wafer. $|A_1A_2|$ varies along the vertical diameter of the wafer and it characterizes the shape of the wafer along the vertical diameter in the absence of the deformation. Therefore, Eq.13 or Eq.8 give the variation of the shape of the wafer.

The major advantage of the method according to the present invention is that the mathematical steps are easy to carry out. When the measurement data taken in Cartesian coordinates are mapped into polar coordinates and M, M', M", S and E are chosen to be vectors or column matrices, the problem is decomposed into simpler problems of lower dimension. Thus, instead of solving a system of $N_\theta \times N_r$, which is in general very complex, we choose to solve $N_r$ independent systems of $N_\theta$ equations. Furthermore, in polar coordinates, it is possible that both LU factors and their inverses are sparse, as shown in Equation 13 above. In storing the L, U matrices and their inverses, only the address of the elements that have a value of 1 need to be known. The storage of these matrices takes much less memory than storage of Fourier harmonics for the same dimensions.

Although the invention has been described with respect to a preferred version and embodiment thereof, it will be understood by those skilled in the art that the foregoing and various other changes, omissions and deviations in the form and detail thereof may be made without departing from the spirit and scope of this invention.

What is claimed is:

1. A method of measuring the surface profile of an object to develop a surface profile map for the object's surface without station-induced errors, the method comprising the steps of:

1) providing an object having a surface whose profile is to be measured;
2) providing a measurement device having an object holder, a first distance sensor and a second distance sensor spaced apart from the first distance sensor by a known distance;
3) holding the object with the object holder in a first orientation with respect to the object holder;
4) disposing the object in the first orientation with respect to the object holder between the first and second distance sensors so that the object's surface is facing the first distance sensor;
5) measuring the distance between the first distance sensor and the object's surface in the first orientation with respect to the object holder for a plurality of points over the object's surface in a first coordinate pattern of known orientation with respect to the object holder to obtain a first matrix of measurement points;
6) rotating the object about a first axis which is substantially normal to the object's surface so as to hold the object with the object holder in a second orientation with respect to the object holder, wherein said rotation is represented by a rotation matrix;
7) disposing the object in the second orientation with respect to the object holder between the first and second distance so that the object's surface is facing the first distance sensor;
8) measuring the distance between the first distance sensor and the object's surface in the second orientation with respect to the object holder for a plurality of points over the object's surface in second coordinate pattern of known orientation with respect to the object holder to obtain a second matrix of measurement points;
9) obtaining a difference matrix by subtracting the first matrix from the second matrix;
10) removing the rotation matrix by applying an inverse matrix to the difference matrix, wherein the inverse matrix is the inverse of the difference between the rotation matrix and an identity matrix;
11) flipping the object about a second axis which is substantially perpendicular to the first axis so as to hold the object with the object holder in a third orientation with respect to the object holder;
12) disposing the object in the third orientation with respect to the object holder between the first and second distance so that object's surface is facing the second distance sensor;
13) measuring the distance between the second distance sensor and the object's surface in the third orientation with respect to the object holder for a plurality of points over the object's surface in third coordinate pattern of known orientation with respect to the object holder to obtain a third matrix of measurement points; and
14) obtaining the surface map of the object's surface by applying the selected measurement points of the third matrix to the difference matrix as processed in step 10.

2. The method of claim 1 wherein the first and second matrices are column matrices.

3. The method of claim 1 wherein the first and second matrices are vectors.

4. The method of claim 1 wherein the first axis is substantially parallel to a vertical plane.

5. The method of claim 1 wherein the third matrix is a column matrix.

6. The method of claim 1 wherein the third matrix is a vector.

7. The method of claim 1 wherein the removing of the rotation matrix in step 10 comprises the step of LU decomposing of the difference between the rotation matrix and an identity matrix, with L being a lower triangular matrix and U being an upper triangular matrix.

8. The method of claim 7 wherein the L, U matrices and the inverses matrix are pre-computed.

9. The method of claim 1 wherein the measurement points in step 5 and step 8 are sampled at a plurality of nodes on a rectangular grid of Cartesian coordinates.

10. The method of claim 1 wherein the measurement points in step 5 and step 8 are sampled at a plurality of nodes on a square grid of Cartesian coordinates.

11. The method of claim 1 wherein the measurement points in step 5 and step 8 are sampled at a plurality of nodes on a polar grid.

12. The method of claim 1 wherein the first distance sensor and the second distance sensor comprise respective optical sensors.

13. A method of separating station-induced errors caused by an object holder from measurements of an object having a first surface using a first sensor and a second sensor to measure the first surface when the object is placed in a first plane substantially parallel to the first surface, and wherein the first sensor and the second sensor are located on the opposite sides of the first plane along a first line substantially perpendicular to the first plane, said method comprising the steps of:

1) measuring with the first sensor a multiplicity of first points on the first surface of the measured object at a first orientation to obtain a first matrix (M) of measurement points in polar coordinates having nodes on a plurality of concentric circles, each number representing the distance between a first point and the first sensor; said first matrix (M) containing a surface matrix (S) and a station-induced error matrix (E);

2) rotating the measured object independently of the object holder about a first axis substantially parallel to the first plane by a first angle ($\alpha$) to placed the measured object at a second orientation, thereby generating a rotation matrix (R);

3) measuring with the first sensor a multiplicity of second points on the first surface of the measured object at the second orientation to obtain a second matrix (M') of measurement points, each representing the distance between a second point and the first sensor, each second point having a corresponding first points;

4) obtaining a first difference matrix (M'-M) between the second matrix (M') and the first matrix (M), thereby obtaining the product of a second difference matrix (R-I) and the surface matrix (S);

5) flipping the measured object about a second axis substantially perpendicular to the first axis by 180 degrees to place the object at a third orientation;

6) measuring with the second sensor the first surface of the measured object at the third orientation to obtain a multiplicity of third points to obtain a third matrix (M") of measurement points, each third point having a corresponding second point;

7) obtaining a first average value (s1) of a select measurement point (m1") in the third matrix and the corresponding measurement point (m1) in the first matrix;

8) removing the second difference matrix (R-I) from the surface matrix (S) by LU decomposing the second difference matrix, wherein L is a lower triangular matrix and U is an upper triangular matrix, and multiplying the first inverse matrix ($L^{-1}$) to the first difference matrix (M'-M), wherein the first inverse matrix ($L^{-1}$) is the inverse of the lower triangular matrix (L);

9) obtaining an auxiliary matrix ($\lambda$) from the product of the first inverse matrix and the first difference matrix;

10) obtaining a remaining surface component ($S_r$) for a circle from the auxiliary matrix ($\lambda$), the second inverse matrix ($U^{-1}$) and the first average value (s1), wherein the second inverse matrix is the inverse of the upper triangular matrix (U);

11) repeating steps 7 to 11 for all circles of the measured points.

14. The method of claim 13 wherein the first inverse matrix ($L^{-1}$) and the second inverse matrix ($U^{-1}$) are pre-computed.

15. A method of removing station-induced errors caused by an object holder from measurement data of an object held by the object holder obtained by a device, said method comprising the steps of:

1) measuring the object at a first orientation with respect to the object holder to obtain a first matrix of measurement points containing the station-induced errors and the map of the proper shape of the object's surface;

2) rotating the object independently of the holding device to place the object at a second orientation with respect to the object holder;

3) measuring the object at the second orientation to obtain a second matrix of measurement points containing station-induced errors and the surface map of the object as processed by a rotation transformation represented by a rotation matrix;

4) removing the station-induced errors from the measurement data by subtracting the first matrix from the second matrix;

5) flipping the object and measuring the object at a third orientation with respect to the object holder to obtain a third matrix of measurement points;

6) obtaining the surface characteristics at selected measurement points from the first matrix and the third matrix; and 7) removing the rotation transformation by applying an inverse of the difference between a rotation matrix and an identity matrix to the difference of the second matrix and the first matrix.

* * * * *